United States Patent
Hamilton et al.

(10) Patent No.: US 6,769,317 B1
(45) Date of Patent: Aug. 3, 2004

(54) CORE SAMPLING APPARATUS

(76) Inventors: Edward M. Hamilton, 121 Donaleen Ct., Martinez, CA (US) 94533; Jindrich Dokonal, 22027 McClellan Rd., Cupertino, CA (US) 95014

( * ) Notice: Subject to any disclaimer, the term of this patent is extended or adjusted under 35 U.S.C. 154(b) by 0 days.

(21) Appl. No.: 10/295,546

(22) Filed: Nov. 15, 2002

(51) Int. Cl.[7] ................................................ G01N 1/04
(52) U.S. Cl. ................................ 73/864.44; 73/864.51; 73/864.91
(58) Field of Search ............ 73/864.41, 864.42–864.45, 73/864.51, 864.52, 864.53, 864.55, 864.59, 864.82, 864.83, 864.91, 863.31; 83/405; 175/20, 50, 58, 84, 259, 403; 221/80

(56) References Cited

U.S. PATENT DOCUMENTS

| | | | | |
|---|---|---|---|---|
| 3,595,086 A | * | 7/1971 | Bonnet et al. ............ | 73/864.01 |
| 4,563,789 A | * | 1/1986 | Berfield ................... | 15/323 |
| 4,989,678 A | * | 2/1991 | Thompson ............... | 175/20 |
| 5,088,562 A | * | 2/1992 | Shields ..................... | 172/22 |
| 5,686,673 A | * | 11/1997 | Kabis ...................... | 73/863.31 |
| 5,931,236 A | | 8/1999 | Mahlum et al. .......... | 175/20 |
| 6,009,958 A | | 1/2000 | Nakata et al. ............ | 175/20 |
| 6,125,948 A | * | 10/2000 | David et al. .............. | 175/58 |
| 2003/0089526 A1 | * | 5/2003 | Beeker .................... | 175/58 |

FOREIGN PATENT DOCUMENTS

JP          04290944 A    * 10/1992 .......... G01N/3/00

* cited by examiner

*Primary Examiner*—Hezron Williams
*Assistant Examiner*—David A. Rogers
(74) *Attorney, Agent, or Firm*—Jack Lo

(57) ABSTRACT

A core sampling apparatus is comprised of a tubular punch, a storage container, and a press. The punch is comprised of a plurality of generally parallel metal sample tubes for being forced into a ground material. The storage container is comprised of a plurality of parallel storage tubes, a cap, and a lock nut. The filled punch is pushed into the storage tubes for encapsulation, and cap is secured against the open end of the storage container by the lock nut. The material samples are ejected from the storage container with an extraction tool with prongs attached to the press. Prongs on the extraction tool are inserted into the punch through breakable ends of the storage tubes, and the material samples are pushed out through breakable ends of the cap by the prongs into a collection vial.

16 Claims, 6 Drawing Sheets

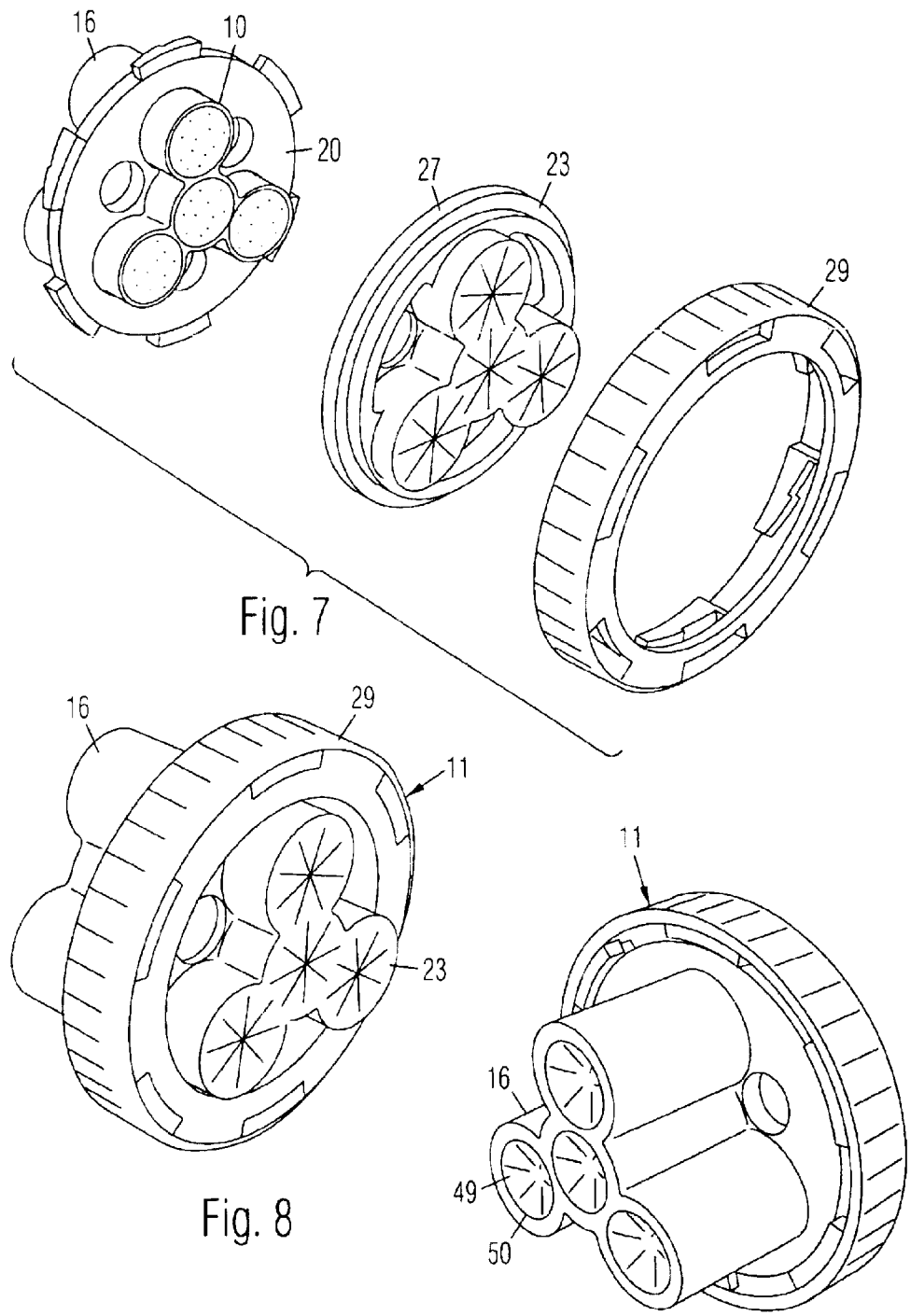

CORE SAMPLING APPARATUS

BACKGROUND OF THE INVENTION

1. Field of the Invention

The invention broadly relates to devices for taking material samples from the ground for storage prior to analysis.

2. Prior Art

Testing for volatile contaminants in the ground typically involves taking soil samples prior to analysis. Ground material is extracted by forcing a tubular core sample liner into the ground by a drilling rig, hand auger, percussion technique, or pushing by hand. As the liner is forced into the ground, ground material is forced into the hollow liner. After the liner is retrieved, ground material samples are taken from inside the liner.

Due to inadequate soil collection and handling techniques commonly used in the environmental industry that produce inaccurate and irreproducible results, the Environmental Protection Agency (EPA) developed EPA method 5035 to outline proper ground material sampling protocols for volatile organic compounds. For each volatile soil test, the EPA method requires a minimum of two samples to be taken at each geographic sampling point, one for high level contamination and one for low level contamination, and recommends a third sample as a low level replicate. Air cannot be introduced into the samples during collection. The samples cannot be parsed or subdivided during or after collection. The low level sample is considered "spent" by its laboratory analysis, therefore a replicate sample is recommended. If a second volatile test is desired, at least one additional sample is required and a duplicate is recommended. Therefore, for each geographic sampling point, two to five samples may be collected.

Sampling devices known in the industry cannot provide true replicate samples (samples as identical to each other as nature allows), nor can they provide duplicate samples (samples from the same geographical proximity) simultaneously with a single coring motion.

A sampler sold under the trademark "ENCORE" by EnNovative Technologies in Green Bay, Wis., takes only one sample. SoilCore in Wyoming sells a sampler that takes two samples at same geographic proximity. However, each sample requires a separate coring action because the samples fill opposite ends of a divided coring tube. The two samples are not replicates because their coring tubes are of different lengths. The EnNovative Technologies and SoilCore samplers are made of a tough glass-filled plastic, but they are still not strong enough to be pounded into dry, compacted soils for taking samples. Their walls are also too thick for penetrating the hard materials.

Another sampler made by US Oil Company in Kimberly, Wis., is comprised of a plastic syringe for taking soft samples. The samples are ejected into collection vials after being extracted from the ground. Each sampler can only take one sample, which must be weighed in the field. The syringes cannot take samples from dry and hard soils.

BRIEF SUMMARY OF THE INVENTION

Accordingly, the objects of the present core sampler apparatus are:

- to simultaneously take a plurality of substantially identical ground material samples from the same geographic proximity;
- to simultaneously take plural samples from a conventional core sample liner;
- to be able to take samples from hard materials, such as dry and compacted soil;
- to avoid introducing air into the samples during the collection process;
- to seal the samples inside a storage container; and
- to dispense the samples from the storage container into collection vials with reduce air exposure.

The present core sampling apparatus is comprised of a tubular punch, a storage container, and a press. The punch is comprised of a plurality of parallel metal sample tubes for being forced by into a ground material. The storage container is comprised of a plurality of parallel storage tubes, a cap, and a lock nut. The filled punch is pushed into the storage tubes by the press for encapsulation, and cap is secured against the open end of the storage container by the lock nut. The material samples are ejected from the storage container with an extraction tool with prongs attached to the press. Prongs on the extraction tool are inserted into the punch through breakable ends of the storage tubes, and the material samples are pushed out through breakable ends of the cap by the prongs.

BRIEF DESCRIPTION OF THE SEVERAL VIEWS OF THE DRAWING

FIG. 7 is an exploded view of the storage container, with the filled punch positioned in the storage tubes of the storage container.

FIG. 8 is a perspective end view of the storage container fully assembled.

FIG. 9 is a perspective opposite end view of the storage container fully assembled.

DETAILED DESCRIPTION OF THE INVENTION

Figure 1:
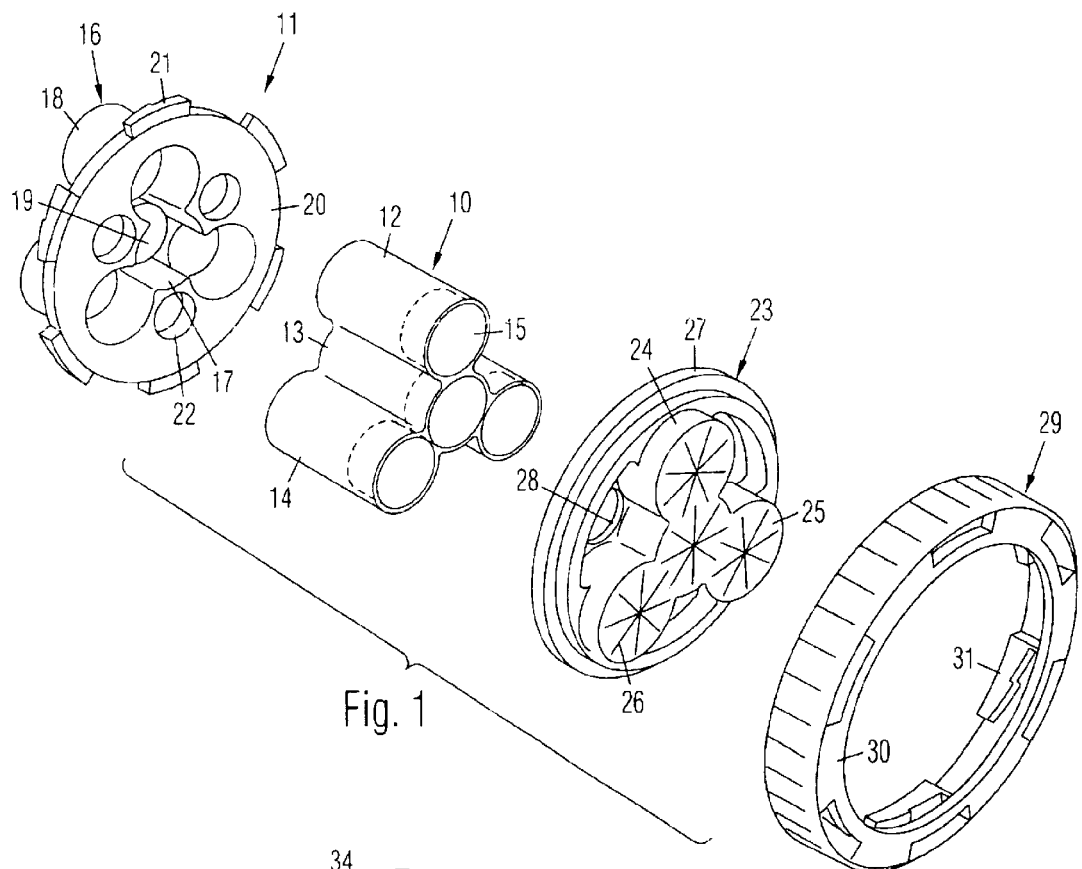
FIG. 1 is a perspective exploded view of a storage container and a tubular punch.

FIG. 1: A preferred embodiment of the present core sampling apparatus is shown in an exploded view in FIG. 1. It is comprised of a tubular punch 10 and a storage container 11. Punch 10 is comprised of a plurality of generally parallel metal sample tubes 12 attached together. Sample tubes 12 may be integrally formed together, or they may be separate tubes connected together by a connecting device, such as a clamp, a strap, etc. Sample tubes 12 may be round as shown, or they may have another cross-sectional shape, such as polygonal, oval, elliptical, etc.

In this example, there is a central sample tube 13 surrounded by three peripheral sample tubes 14, but other arrangements are possible. The example shown includes 16.5 mm outside diameter tubes for taking samples from a conventional 2 inch×6 inch core sample liner (not shown) filled with ground material. Sample tubes 12 have open opposite ends, and snug-fitting movable pistons 15 positioned adjacent respective first ends. Punch 10 is preferably made of a material, such as aluminum alloy or steel, which is hard enough for being pressed or hammered into hard materials, such as dry and compacted soil.

Storage container 11 is comprised of a plurality of overlapping parallel storage tubes 16 in the same arrangement as sample tubes 12 in punch 10. In this example, storage tubes 16 include a central storage tube 17 surrounded by peripheral storage tubes 18. Storage tubes 16 have breakable closed ends 19 opposite overlapping open ends. Closed ends 19 are comprised of inwardly directed cylindrical projections with outer diameters slightly smaller than the inner diameters of sample tubes 12. A circular storage container flange 20 is attached around the open ends of storage tubes 16. Stepped and angled locking tabs 21 are arranged radially around the circumference of flange 20. A plurality of storage container flange holes 22 matching the number of peripheral sample tubes 14 are radially offset between peripheral storage tubes 18 on flange 20.

Storage container is also comprised of a cap 23 with a plurality of overlapping parallel cap tubes 24 in the same arrangement as storage tubes 16. Cap tubes 24 have breakable closed ends 25 and overlapping open ends (not shown). Weakened areas 26 preferably comprised of star-shaped patterns are arranged on closed ends 25 for enabling breakage. A circular cap flange 27 is attached around the open ends of cap tubes 24. A plurality of cap flange holes 28 are radially offset between cap tubes 24.

Storage container is also comprised of a lock nut 29, which is comprised of a ring 30 with stepped and angled locking tabs 31 on an inner surface for mating with locking tabs 21 on storage container flange 20.

Sample tubes 12 are sized to fit snugly into storage tubes 16 of storage container 11. The interiors of storage tubes 16 are arranged to seal around the corresponding ends of sample tubes. Sample tubes 12 are longer than storage tubes 16, so that sample tubes 12 project out of open ends of storage tubes 16. Cap 23 is sized to fit snugly onto the projecting ends of sample tubes 12. The interiors of cap tubes 24 are also arranged to seal around the corresponding ends of sample tubes 12. Storage container flange 20 and cap flange 23 have flat mating surfaces that provide yet another seal when lock nut 29 is installed around flanges 20 and 23.

Figure 2:
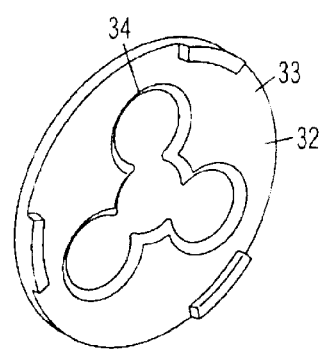
FIG. 2 is a perspective view of a cleaning ring for the punch in FIG. 1.

FIG. 2: The core sampling apparatus is also comprised of a cleaning ring 32 shown in FIG. 2. Cleaning ring 32 is comprised of a plate 33 with a hole 34 which is shaped to substantially match the cross-sectional shape of punch 10 (FIG. 1).

Figure 3:
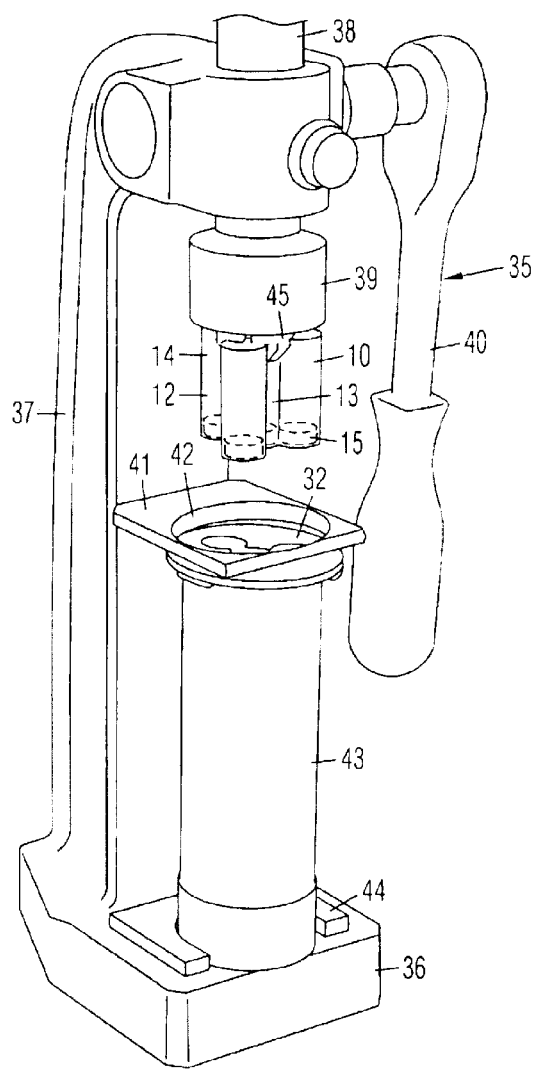
FIG. 3 is a perspective view of the punch held in the grip of a press, and the cleaning ring positioned on top of a conventional core sample liner.

FIGS. 3–9: As shown in FIG. 3, the core sampling apparatus is also comprised of a press 35 that includes a base 36, an arm 37 extending up from base 36, a movable vertical shaft 38 attached to the top end of arm 37, a gripping tool 39 attached to the bottom end of shaft 38, and a crank 40 attached to the top end of arm 37 and arranged to move shaft 38 up or down. A support platform 41 with a hole 42 is positioned between gripping tool 39 and base 36, and is preferably attached to arm 37.

The process of taking and encapsulating samples is shown in FIGS. 3–9. In FIG. 3, a conventional tubular core sample liner 43 filled with ground material drilled from underground is positioned vertically within a holding bracket 44 on, base 36. Cleaning ring 32 is positioned on an open end of core sample liner 43. Support platform 41 is positioned over cleaning ring 32. Punch 10 is held in gripping tool 39. In this example, gripping tool 39 includes three jaws 45 that grip the sides of central sample tube 13 between peripheral sample tubes 14. Punch 10 is arranged to position pistons 15 on the bottom.

Figure 4:
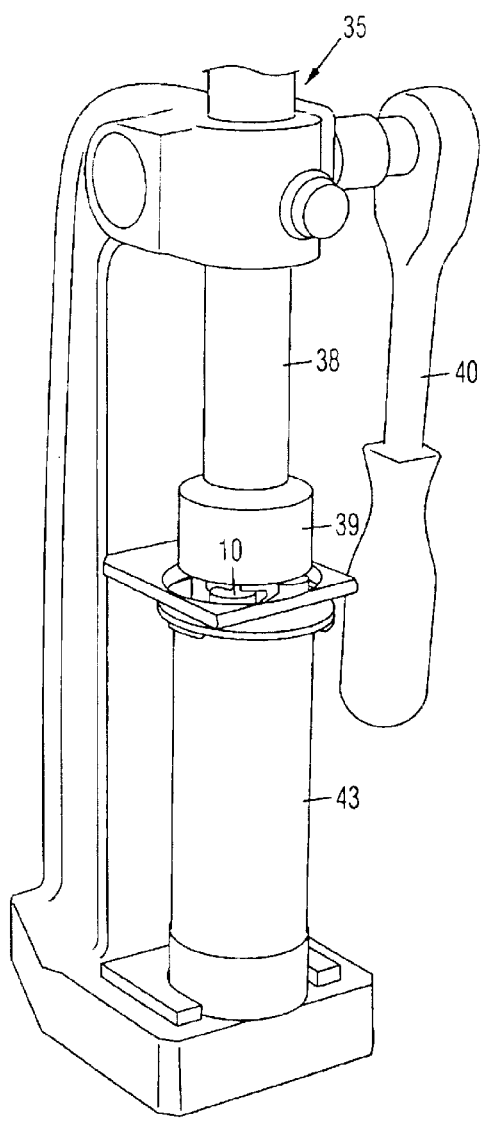
FIG. 4 is a perspective view of the punch pushed into the core sample liner.

In FIG. 4, crank 40 is moved to move punch 10 downward through the hole in cleaning ring 32 into the material inside core sample liner 43. Punch 10 is made of a hard enough metal to cut into a variety of ground materials, including relatively hard ground materials such as dry and compacted soil. Since pistons 15 are initially positioned at the bottom of sample tubes 12, there is no air space between pistons 15 and the top of the ground material in core sample liner 43. As punch 10 is pushed into the ground material, sample tubes 12 of punch 10 are gradually filled with ground material and pistons 15 are pushed upward until they contact gripping tool 39. No air is pushed into the material samples during the collection process.

Figure 5:
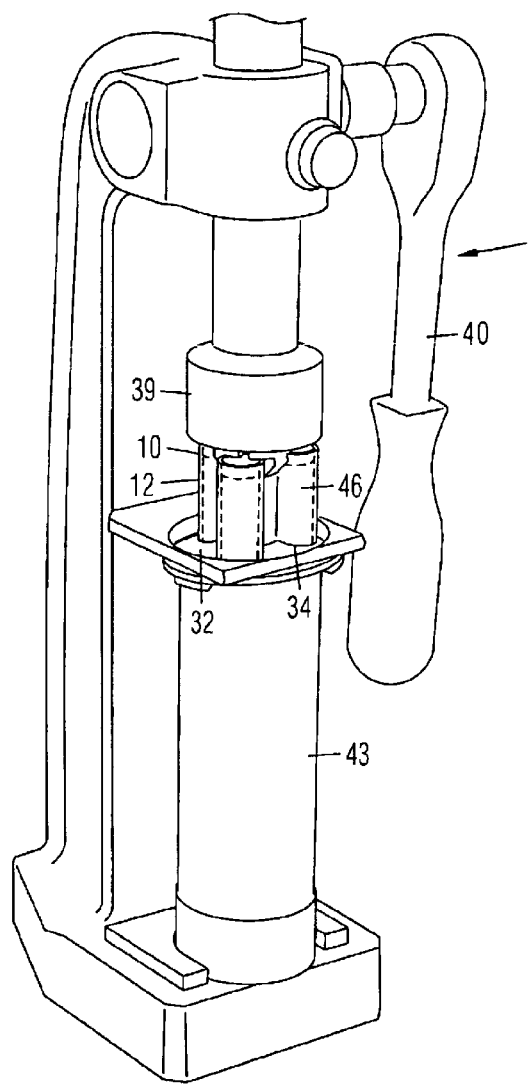
FIG. 5 is a perspective view of the punch being withdrawn from the core sample liner through the cleaning ring.

In FIG. 5, crank 40 is rotated to move punch 10 upward and out of core sample liner 43 through cleaning ring 32. Since the top end of core liner 43 is covered by cleaning ring 32, lose material is prevented from being pulled out of core liner 43. The sides of punch 10 are wiped clean by the rims of hole 34 in cleaning ring 32. Pistons 15 have been moved to the top ends of sample tubes 12 by the upwardly advancing material samples 46. The upward travel of pistons 15 is limited by gripping tool 39. Pistons 15 keep the tops of material samples 46 compacted to avoid air space, and to prevent material samples 46 from spilling out the top of punch 10. Alternatively, punch 10 may be pushed into the material manually without press 35.

Figure 6:
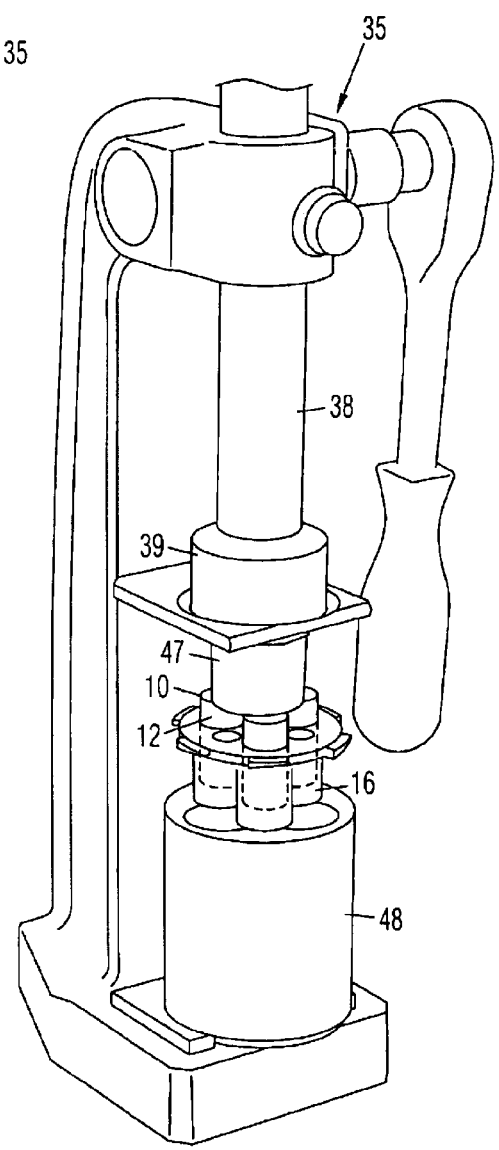
FIG. 6 is a perspective view of the punch being pushed into the storage container.

In FIG. 6, punch 10 is pushed into storage tubes 16 by hand or with a pressing tool 47 attached to shaft 38 of press 35. Punch 10 is inserted with the piston end first. The projections (not shown) at the inner ends of storage tubes 16 advance pistons 15 (FIG. 1) slightly upward to extrude the material samples slightly from the outer end of punch 10. The extruded material samples are shaved off with a straight edge, such as a blade, after gripping tool 39 is detached from punch 10. Therefore, sample tubes 12 of punch 10 are substantially filled with material samples and air pockets are avoided. In this example, due to the limited downward travel of shaft 38, a collection vial holder 48 is positioned under storage tubes 16 to position storage tubes 16 closer to the bottom of shaft 38.

In FIG. 7, punch 10 is fully inserted into storage tubes 16. Since punch 10 is longer than storage tubes 16, a portion of punch 10 remains outside storage tubes 16. Cap 23 is arranged to be placed against the end of punch 10, and lock nut 29 is arranged to be screwed onto flanges 20 and 27. In FIG. 8, cap 23 is secured on storage tubes 16 by lock nut 29 to fully encapsulate the material samples. Preferably, the opposite ends of punch 10 are respectively sealed by ridges (not shown) inside storage tubes 16 and cap tubes 24. The flat mating surfaces of flanges 20 and 27 (FIG. 7) provide a further seal. In FIG. 9, an opposite end perspective view of storage container 11 is shown to illustrate concave ends 49 of storage tubes 16, which have weakened rims 50 for being sheared open. Concave ends 49 form inward projections 19 (FIG. 1) on the insides of storage tubes 16.

Figure 10:
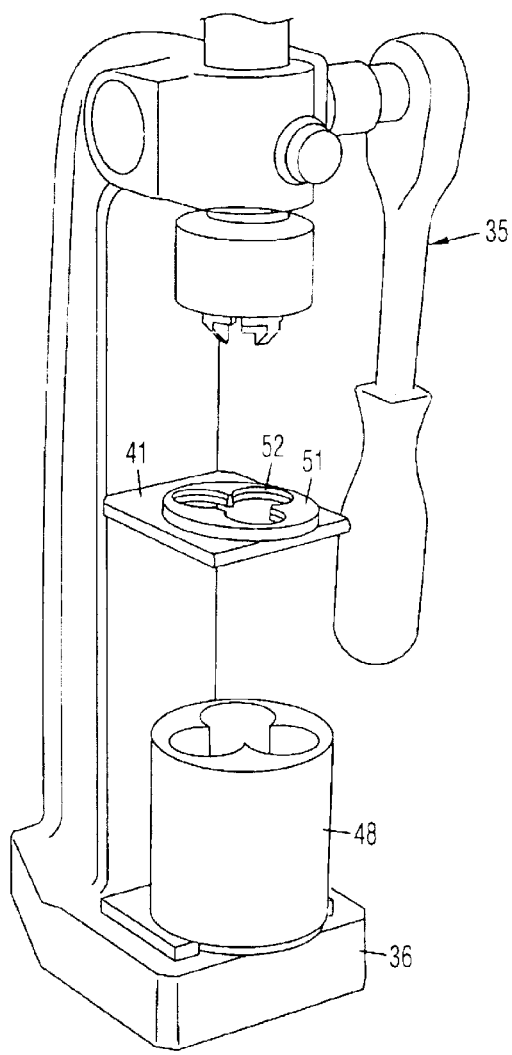
FIG. 10 is a perspective view of the press arranged for ejecting material samples from the storage container.
Figure 11:
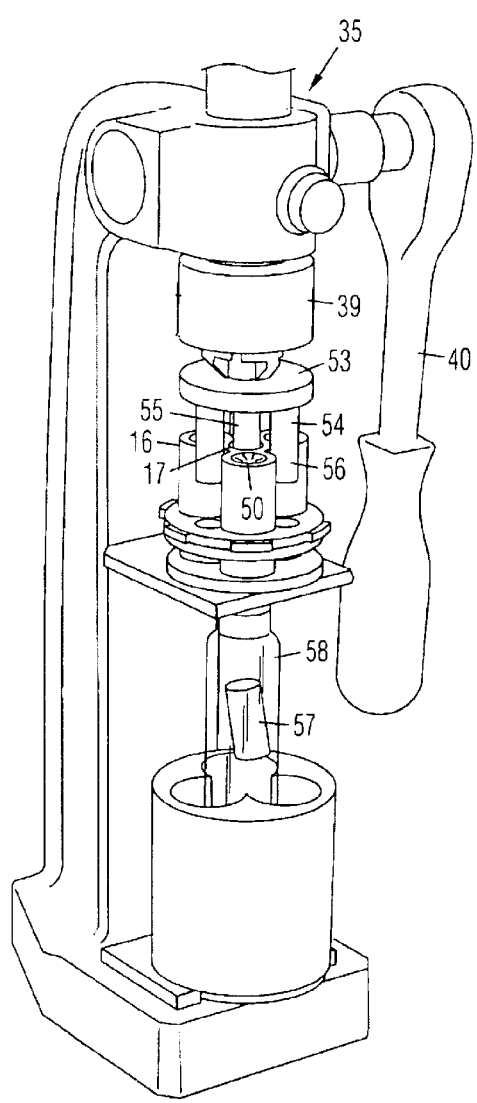
FIG. 11 is a perspective view of a material sample being ejected from the center storage tube of the storage container.
Figure 12:
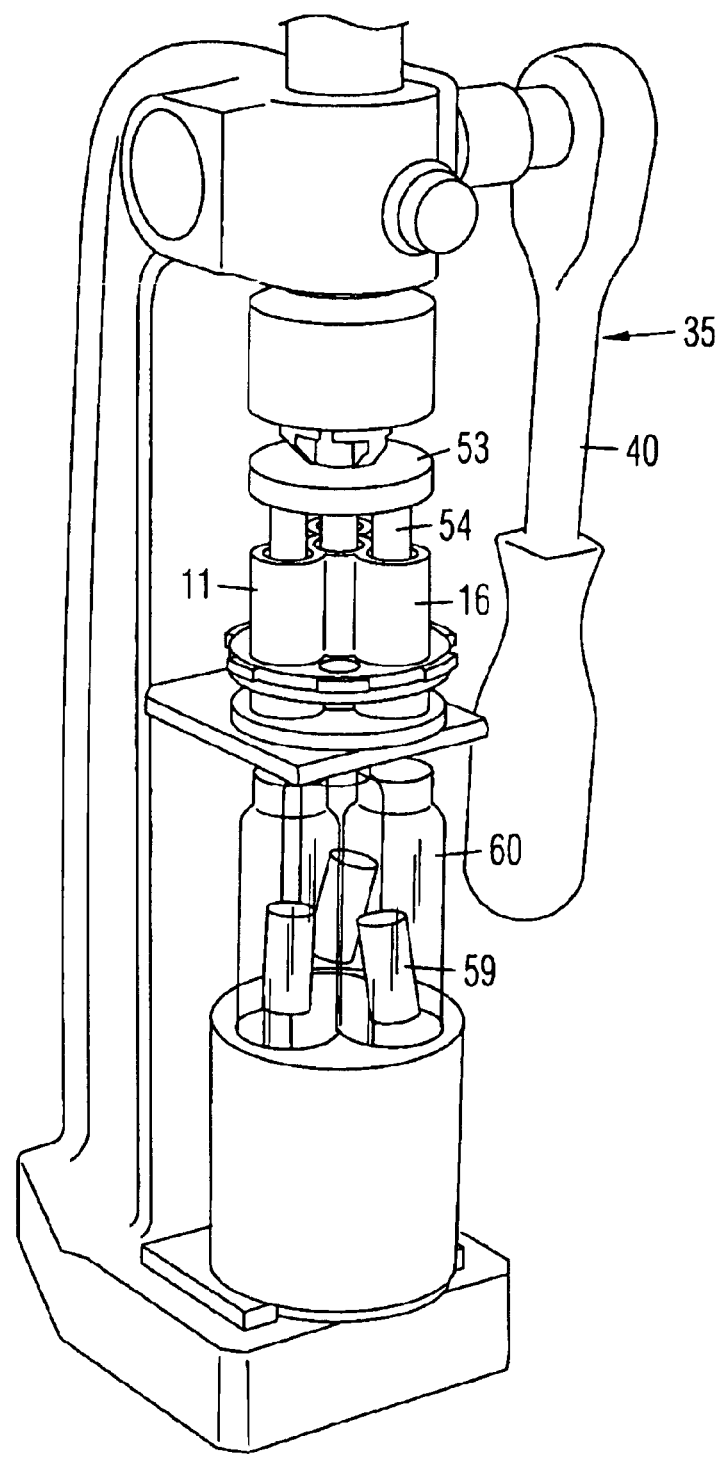
FIG. 12 is a perspective view of the material samples being ejected from the periphery storage tubes of the storage container.

FIGS. 10–12: The process of extracting material samples is shown in FIGS. 10–12. In FIG. 10, vial holder 48 is positioned on base 36 of press 35. A support ring 51 with a hole 52 is positioned on support platform 41. Hole 52 is preferably shaped to substantially match the cross-sectional shape of storage tubes 16 (FIG. 1), but is slightly larger to allow the ends of storage tubes 16 to pass through to avoid contamination of platform 41 by the material samples during extrusion.

In FIG. 11, an extraction tool 53 with a plurality of vertical prongs 54 is attached to gripping tool 39 on press 35. Prongs 54 are arranged to align with storage tubes 16, and have diameters slightly smaller than the inner diameters of sample tubes 12 (FIG. 1) which are now inside storage tubes 16. Storage container 11 is positioned on support ring 41 with cap 23 on the bottom and storage tubes 16 on top. Storage tubes 16 are aligned with hole 52. Extraction tool 53 is positioned to align a center prong 55 with center storage tube 17, and to position peripheral prongs 56 between peripheral storage tubes 16. Crank 40 is operated to move extraction tool downward, and thus center prong 55 against breakable concave end 49 (FIG. 9) of center storage tube 17. Weakened rim 50 of concave end 49 (FIG. 9) is broken inward and pushed against piston 15 (FIG. 1) inside center sample tube 17. Material sample 57 in center sample tube 17 is pushed downward by the corresponding piston 15. Closed end 25 (FIG. 1) of the center cap tube is forced open at weakened area 26 (FIG. 1) by the advancing sample material, which is continued to be forced down by the piston until it is ejected from storage container into a collection vial 58. Piston 15 is retained inside storage container 11 after material sample 57 is ejected.

In FIG. 12, extraction tool 53 is retracted and prongs 54 are aligned with all storage tubes 16 of storage container 1, and the extraction process is repeated to eject material samples 59 into collection vials 60 from peripheral sample tubes 14 in punch 10. Therefore, four substantially identical material samples are produced. A two-step extraction process is disclosed in this example because the collection vials shown have larger diameters than the sample tubes in the punch, such that four of the exemplar collection vials cannot be simultaneously aligned with the sample tubes.

Alternatively, all four collection vials can be placed together, but not under the storage container. All four samples can be ejected simultaneously, and chutes can be provided to direct the samples into all four collection vials. Also, smaller diameter collection vials can be provided, so that all four can be placed under the storage container to receive all four samples directly at the same time.

Although the foregoing description is specific, it should not be considered as a limitation on the scope of the invention, but only as an example of the preferred embodiment. Many variations are possible within the teachings of the invention. For example, different attachment methods, fasteners, materials, dimensions, etc. can be used unless specifically indicated otherwise. The relative positions of the elements can vary, and the shapes of the elements can vary. Therefore, the scope of the invention should be determined by the appended claims and their legal equivalents, not by the examples given.

We claim:

1. A core sampling apparatus, comprising:
   a tubular punch comprising a plurality of generally parallel sample tubes laterally attached together wherein said sample tubes are arranged for being simultaneously inserted in a material and taking a plurality of material samples in proximity to each other, said sample tubes including first open ends for admitting said material samples and second open ends for exhausting air from said sample tubes when said material samples are being admitted to avoid forcing air into said material samples; and
   a cleaning ring comprised of a plate with a hole shaped to substantially match a cross-sectional shape of said punch, wherein when said punch is pushed through said hole in said cleaning ring, an exterior of said punch is wipe by said cleaning ring.

2. The core sampling apparatus of claim 1, wherein said sample tubes include a central round sample tube surrounded by peripheral round sample tubes which are directly attached to said central round sample tube, and all of said sample tubes are identical in diameter.

3. The core sampling apparatus of claim 1, wherein said sample tubes include a central sample tube surrounded by peripheral sample tubes, said sample tubes each having a 16.5 mm diameter for sliding inside a 2 inch diameter core sample liner filled with said material.

4. The core sampling apparatus of claim 1, further including movable pistons respectively positioned in said sample tubes for helping retain said material samples in said sample tubes during collection, wherein said pistons are initially positioned at said first open ends of said sample tubes for avoiding trapping air between said pistons and said material samples.

5. A core sampling apparatus, comprising:
   a tubular punch comprising a plurality of generally parallel sample tubes laterally attached together, wherein said sample tubes include open ends, said sample tubes are arranged for being simultaneously inserted in a material and taking a plurality of material samples in proximity to each other;
   a storage container comprised of a plurality of laterally overlapping parallel storage tubes arranged to align with said sample tubes in said punch;
   a cap with a plurality of laterally overlapping parallel cap tubes arranged to align with said storage tubes in said punch;
   wherein when said sample tubes are inserted into said storage tubes, the interiors of said storage tubes are arranged to seal corresponding ends of said sample tubes, said samples tubes are longer than said storage tubes, so that said sample tubes project from open ends of said storage tubes; and
   when said cap is positioned against projecting ends of said sample tubes, interiors of said cap tubes are arranged to seal said projecting ends of said sample tubes.

6. The core sampling apparatus of claim 5, wherein said sample tubes include a central sample tube surrounded by peripheral sample tubes.

7. The core sampling apparatus of claim 5, wherein said storage tubes include breakable closed ends opposite said open ends, said closed ends comprising inwardly directed cylindrical projections with outer diameters smaller than inner diameters of said sample tubes, said cylindrical projections are arranged to project into said sample tubes for pushing against said material samples, said cap tubes comprising breakable closed ends opposite open ends and configured for breaking under pressure and releasing said material samples.

8. The core sampling apparatus of claim 5, further including a cleaning ring comprising a plate with a hole shaped to substantially match a cross-sectional shape of said punch, wherein when said punch is pushed through said hole in said cleaning ring, an exterior of said punch is wiped by said cleaning ring.

9. The core sampling apparatus of claim 5, further including:
   a circular storage container flange attached around said open ends of said storage tubes;
   a circular cap flange attached around open ends of said cap tubes; and
   a lock nut comprising a ring arranged to surround and tighten together said storage container flange and said cap flange.

10. The core sampling apparatus of claim 5, further including:
   a press;
   a gripping tool arranged to be attached to said press to grip said punch for pushing said punch into said material when said material is positioned under said gripping tool, and withdrawing said punch from said material, and when said punch is filled with said material samples, said press is arranged to push said punch into said storage tubes; and
   an extraction tool comprising a plurality of parallel prongs, wherein said extraction tool is arranged to be attached to said press in alignment with said sample tubes in said punch for pushing out said material samples through said breakable ends of said storage container.

11. The core sampling apparatus of claim 5, further including:
   a press comprising a base, an arm extending up from said base, a vertically movable shaft at a top end of said arm, and a crank connected to said shaft and arranged to move said shaft vertically;
   a platform positioned between said shaft and said base, wherein said platform is arranged to support said storage container, said platform comprising a hole arranged under said storage container;
   a gripping tool arranged to be attached to said shaft to grip said punch and push said punch into said material when said material is positioned on said base, and withdrawing said punch from said material, and when said punch is filled with said material samples, said press is arranged to push said punch into said storage tubes; and
   an extraction tool comprising a plurality of parallel prongs, wherein said extraction tool is arranged to be attached to said shaft in alignment with said sample tubes in said punch when said storage container is positioned on said platform, said extraction tool is arranged for pushing out said material samples through said breakable ends of said storage container.

12. The core sampling apparatus of claim 11, further including:
   a circular storage container flange attached around said open ends of said storage tubes;
   a circular cap flange attached around open ends of said cap tubes; and
   a lock nut comprised of a ring arranged to surround and tighten together said storage container flange and said cap flange; and
   wherein said storage tubes include a central storage tube surrounded by peripheral storage tubes, and said cap tubes include a central cap tube surrounded by peripheral cap tubes, said storage container flange includes a plurality of storage container flange holes radially offset between said peripheral storage tubes, and said cap flange includes a plurality of cap flange holes radially offset between said cap tubes, said storage container flange holes and said cap flange holes are aligned for passing said prongs of said extractor when said prongs are radially offset from said peripheral storage tubes.

13. A core sampling apparatus, comprising:
   a tubular punch comprising a sample tube with open ends, wherein said sample tube is arranged for being inserted in a material and taking a material sample;
   a storage container comprised of a storage tube with a breakable closed end and an open end, wherein said storage tube is arranged to receive said sample tube;
   a cap comprising a cap tube with a breakable closed end and an open end, wherein said cap tube is arranged to seal said open end of said storage tube when said sample tube is positioned in said storage tube; and
   wherein said breakable closed end of said storage tube and said breakable dosed end of said cap tube are arrange to break open for releasing said material sample from said sample tube.

14. The core sampling apparatus of claim 13, further including:
   a press comprising a base, an arm extending up from said base, a vertically movable shaft at a top end of said arm, and a crank connected to said shaft and arranged to move said shaft vertically;
   a platform positioned between said shaft and said base, wherein said platform is arranged to support said storage container, said platform includes a hole arranged under said storage container;
   a gripping tool arranged to be attached to said shaft to grip said punch and push said punch into said material when said material is positioned on said base, and withdrawing said punch from said material, and when said punch is filed with said material sample, said press is arranged to push said punch into said storage tube; and
   an extraction tool comprising a prong, wherein said extraction tool is arranged to be attached to said shaft in alignment with said sample tube when said storage container is positioned on said platform, said extraction tool is arranged for pushing out said material sample through said breakable closed ends of said storage container.

15. A method for taking material samples in proximity to each other from a material, storing said material samples, and extracting said material samples, comprising the steps of:
   providing a punch comprising a plurality of generally parallel sample tubes laterally attached together;
   pushing said punch into said material;
   extracting said punch from said material;
   providing a storage container comprising laterally overlapping parallel storage tubes sized to seal first ends of said sample tubes;
   pushing said punch into said storage container;
   providing a cap comprising laterally overlapping parallel cap tubes sized to seal second ends of said sample tubes;
   sealing said storage tubes with said cap for storage;
   providing an extraction tool comprising a plurality of parallel prongs;
   inserting said prongs of said extraction tool through breakable ends of said storage container; and
   pushing out said material samples from said punch through said storage container.

16. A method for taking material samples in proximity to each other from a material, storing said material samples, and extracting said material samples, comprising the steps of:

providing a punch comprising a plurality of peripheral sample tubes generally attached in parallel around a central sample tube;

pushing said punch into said material;

extracting said punch from said material;

providing a storage container comprising laterally overlapping parallel storage tubes arranged to align with and seal first ends of said sample tubes;

pushing said punch into said storage container;

providing a cap comprising laterally overlapping parallel cap tubes arranged to align with and seal second ends of said sample tubes;

sealing said storage tubes with said cap for storage;

providing an extraction tool comprising a plurality of parallel prongs identical arranged as said sample tubes;

aligning a central prong of said extraction tool with said central sample tube, and radially offsetting peripheral prongs of said extraction tool from said peripheral sample tubes;

inserting said central prong of said extraction tool through a breakable first end of said storage container, and pushing out said material samples from said central sample tube through a second breakable end of said storage container;

aligning said peripheral prongs of said extraction tool with said peripheral sample tubes;

inserting said peripheral prongs of said extraction tool through said breakable first end of said storage container; and pushing put said material samples from said peripheral sample tubes through said second breakable end of said storage container.

\* \* \* \* \*